(12) United States Patent
Xu et al.

(10) Patent No.: US 12,303,411 B2
(45) Date of Patent: May 20, 2025

(54) LEFT VENTRICULAR OUTFLOW TRACT STENT AND DELIVERY SYSTEM

(71) Applicant: NANJING DRUM TOWER HOSPITAL, Jiangsu (CN)

(72) Inventors: Can Xu, Jiangsu (CN); Dongjin Wang, Jiangsu (CN)

(73) Assignee: NANJING DRUM TOWER HOSPITAL, Jiangsu (CN)

( * ) Notice: Subject to any disclaimer, the term of this patent is extended or adjusted under 35 U.S.C. 154(b) by 0 days.

(21) Appl. No.: 18/853,671

(22) PCT Filed: May 16, 2024

(86) PCT No.: PCT/CN2024/093760
§ 371 (c)(1),
(2) Date: Oct. 2, 2024

(87) PCT Pub. No.: WO2025/044305
PCT Pub. Date: Mar. 6, 2025

(65) Prior Publication Data
US 2025/0107909 A1    Apr. 3, 2025

(30) Foreign Application Priority Data
Aug. 29, 2023   (CN) .......................... 202311096513.2

(51) Int. Cl.
*A61F 2/95*      (2013.01)
*A61F 2/915*    (2013.01)

(52) U.S. Cl.
CPC .............. *A61F 2/95* (2013.01); *A61F 2/915* (2013.01); *A61F 2210/0014* (2013.01);
(Continued)

(58) Field of Classification Search
CPC ........ A61F 2/82–945; A61F 2210/0047; A61F 2250/0048; A61F 2250/0042
See application file for complete search history.

(56) References Cited

U.S. PATENT DOCUMENTS

| 6,206,910 B1 | 3/2001 | Berry et al. |
| 2001/0010013 A1 | 7/2001 | Cox et al. |

(Continued)

FOREIGN PATENT DOCUMENTS

| CN | 116327428 A | 6/2023 | |
| WO | WO-9725937 A1 * | 7/1997 | ............... A61F 2/91 |
| WO | WO-2005004750 A1 | 1/2005 | |

*Primary Examiner* — Rebecca S Preston
(74) *Attorney, Agent, or Firm* — Muncy, Geissler, Olds & Lowe, P.C.

(57) ABSTRACT

The present invention discloses a left ventricular outflow tract stent and a delivery system. The left ventricular outflow tract stent includes a stent body, the stent body is composed of a plurality of supporting components arranged along a first path coinciding with a left ventricular outflow tract path, each of the supporting components includes an inverted-V-shaped frame and an inverted-trapezoidal frame, and the inverted-V-shaped frames and the inverted-trapezoidal frames are alternately arranged to form peak regions and valley regions; connecting strips are arranged on the supporting components; and the stent delivery system includes a control component, a delivery catheter, an air bag component, a guide component, and a loading component, the air bag component is connected with the control component through the delivery catheter, the guide component is arranged at an end of the air bag component, away from the delivery catheter, and the loading component is arranged at an end of the guide component away from the air bag component. The control component is configured to control the delivery system to accurately carry and release the stent body on the loading component to a proper position of the left ventricular outflow tract, so that the safety of a minimally invasive surgery is improved.

7 Claims, 10 Drawing Sheets

(52) U.S. Cl.
CPC ............... *A61F 2210/0076* (2013.01); *A61F 2220/0033* (2013.01); *A61F 2230/0023* (2013.01); *A61F 2230/0026* (2013.01); *A61F 2250/001* (2013.01); *A61F 2250/0042* (2013.01); *A61F 2250/0048* (2013.01)

(56) References Cited

U.S. PATENT DOCUMENTS

| | | |
|---|---|---|
| 2005/0038501 A1 | 2/2005 | Moore, Jr. et al. |
| 2008/0033523 A1 | 2/2008 | Gale et al. |
| 2008/0269846 A1* | 10/2008 | Burwell ............... A61N 5/062 607/88 |
| 2009/0209814 A1* | 8/2009 | Saadat ............... B29C 66/1122 428/34.1 |
| 2015/0313732 A1 | 11/2015 | Fulton, III |
| 2016/0262884 A1 | 9/2016 | Lombardi et al. |
| 2017/0079717 A1 | 3/2017 | Walsh et al. |
| 2017/0119450 A1 | 5/2017 | Miyagawa et al. |

\* cited by examiner

LEFT VENTRICULAR OUTFLOW TRACT STENT AND DELIVERY SYSTEM

TECHNICAL FIELD

The present invention relates to the technical field of medical apparatuses, and in particular, to a left ventricular outflow tract stent and a delivery system.

BACKGROUND

Patients suffering from various medical conditions or diseases may require surgical intervention to install implantable medical devices. For example, valvular regurgitation or narrowed calcification of the heart valve leaflet can be treated with the heart valve replacement surgery. The traditional surgical valve replacement surgery requires sternotomy and cardiopulmonary bypass, which may cause serious traumas and discomforts to patients. The traditional surgical valve surgery may also require a long recovery period and may cause life-threatening complications.

An alternative solution of the traditional surgical valve replacement surgery is to use a minimally invasive technology to deliver implantable medical devices. For example, a prosthetic heart valve can be delivered to an implantation site through percutaneous and transluminal delivery. In this method, the prosthetic heart valve can be compressed or coiled onto a delivery cannula to be inserted into the vascular system of a patient, pushed to the implantation site, and then expanded to be deployed at the implantation site. The devices commonly used for entering blood vessels and other positions in the body and implement various functions at these positions include medical cannulas or delivery cannulas, which are suitable for delivering and deploying medical devices (such as prosthetic heart valves, stent grafts, and stents) to selected target sites in the body. When a cannula is guided to a target treatment deployment site and positioned, such a medical device is typically carried in a radially compressed delivery state or configuration in a releasable manner within a distal region of the delivery cannula. However, due to the complexity of individual situations of patients, in actual surgical processes, the release of a stent is easily affected by the internal environment because of the special natures of the heart environments of different patients.

SUMMARY

The purpose of this section is to overview some aspects of embodiments of the present invention and briefly introduce some preferred embodiments. Simplification or omission may be made in this section as well as in the abstract of the specification of the present application and the title of the present invention to avoid blurring the purpose of this section, the abstract of the specification and the title of the present invention, and such simplification or omission cannot be used for limiting the scope of the present invention.

The technical problem to be solved by the present invention is how to improve the safety of a minimally invasive surgery.

In order to solve the above technical problem, the present invention proposes the following technical solution: A left ventricular outflow tract stent is provided, including a stent body, the stent body is composed of a plurality of supporting components arranged along a first path coinciding with a left ventricular outflow tract path, and the supporting components form a ring structure.

Each of the supporting components includes an inverted-V-shaped frame and an inverted-trapezoidal frame, and the inverted-V-shaped frames and the inverted-trapezoidal frames are alternately arranged to form peak regions and valley regions, thereby effectively supporting the left ventricular outflow tract, enabling the blood to flow more freely, reducing blockage and pressure, and effectively avoiding blood flow obstruction.

The left ventricular outflow tract stent further includes connecting strips, and the connecting strips are arranged on the supporting components for storage and fixation of the stent body.

As a preferred solution of the left ventricular outflow tract stent of the present invention, each of the connecting strips is provided with a protrusion, and a material of the protrusions is a magnetic metal, thereby increasing the reliability of storage and fixation of the stent body.

As a preferred solution of the left ventricular outflow tract stent of the present invention, materials of each of the supporting components and each of the connecting strips are both memory metals, inner layers of each of the supporting components and each of the connecting strips are photo-induced deformation layers, outer layers of each of the supporting components and each of the connecting strips are temperature deformation layers, and each of the photo-induced deformation layers and a corresponding temperature deformation layer of the temperature deformation layers are superimposed, thereby enabling the supporting components and the connecting strips to expand more stably to avoid accidents.

A delivery system using the left ventricular outflow tract stent is provided, including a control component, a delivery catheter, an air bag component, a guide component, and a loading component. The control component is configured to control the entire delivery system. The air bag component is connected with the control component through the delivery catheter to control the contraction and expansion of an air bag, so as to preliminarily expand the installation position of the stent in the left ventricle to prevent surgical accidents caused by the tissue force between left ventricular regions affecting the expansion of the stent, so that the stent can be released more safely. The guide component is arranged at an end of the air bag component away from the delivery catheter for guiding the stent. The loading component is arranged at an end of the guide component away from the air bag component for storage and carrying of the stent body.

As a preferred solution of the delivery system of the left ventricular outflow tract stent of the present invention, the loading component includes an optical channel, a first reflecting component, a second reflecting component, and a first medium component. The optical channel is arranged on the guide component. A light source is arranged in the optical channel and acts in the optical channel. The first reflecting component is arranged at the periphery of the optical channel, surrounds the optical channel, and continuously reflects the light in the optical channel. First light-pervious regions are alternately arranged on a surface of the first reflecting component. The second reflecting component is arranged at the periphery of the first reflecting component. A part of the light passes through the second reflecting component and acts on the stent body, and another part of the light is also repeatedly refracted through the second reflecting component and acts on the stent body. A first gap is formed between the second reflecting component and the first reflecting component. The first medium component is arranged in the first gap. The position of the first medium component corresponds to the first light-pervious regions.

As a preferred solution of the delivery system of the left ventricular outflow tract stent of the present invention, a side of the first medium component away from the first light-pervious regions is provided with a magnetic concave layer matched with the protrusion to maintain the stability of the contracted state of the stent body, prevent accidental expansion of the stent body under the action of external forces, and better fix the stent body. A side of the magnetic concave layer close to the first medium component is provided with a reflecting surface to refract the light refracted onto the first medium component again.

As a preferred solution of the delivery system of the left ventricular outflow tract stent of the present invention, the second reflecting component includes a first medium layer and a reflecting cover. The reflecting cover is arranged on a side of the first medium layer close to the optical channel for refraction of light. The reflecting cover is provided with a light inlet end and a light outlet end, and the size of the light inlet end is greater than the size of the light outlet end, thereby enabling the light refracted onto the second reflecting component to better act on the stent body.

As a preferred solution of the delivery system of the left ventricular outflow tract stent of the present invention, a side wall of a reflecting cavity of the reflecting cover is arranged in an arc shape to better refract light.

As a preferred solution of the delivery system of the left ventricular outflow tract stent of the present invention, the light outlet end of the reflecting cover is provided with a diffusion particle layer for refraction of light to achieve an effect of light diffusion, thereby preventing the light from focusing at a fixed position.

The present invention has the following beneficial effects: The stent composed of the plurality of supporting components in a ring structure is arranged to effectively support the left ventricular outflow tract, enable the blood to flow more freely, reduce blockage and pressure, and avoid blood flow obstruction. Furthermore, the control component is configured to control the delivery system to accurately carry and release the stent body on the loading component to a proper position of the left ventricular outflow tract, so that the safety of a minimally invasive surgery is improved.

BRIEF DESCRIPTION OF THE DRAWINGS

In order to more clearly illustrate the technical solutions in the embodiments of the present invention, the accompanying drawings required for the description of the embodiments will be briefly introduced below. Obviously, the accompanying drawings described below are only some embodiments of the present invention. Those of ordinary skill in the art can also obtain other accompanying drawings according to these accompanying drawings without any creative effort. In the accompanying drawings.

In the figures: 1, control component; 2, delivery catheter; 3, air bag component; 4, guide component; 5, loading component; 51, optical channel; 52, first gap; 53, first medium component; 54, magnetic concave layer; 55, second reflecting component; 551, first medium layer; 552, reflecting cover; 553, light outlet end; 554, light inlet end; 56, first reflecting component; 6, stent body; 61, peak region; 62, valley region; 63, connecting strip; a, temperature deformation layer; b, photo-induced deformation layer; and 64, protrusion.

DETAILED DESCRIPTION

To make the above objectives, features and advantages of the present invention more obvious and comprehensible, the specific implementations of the present invention are described in detail below with reference to the accompanying drawings of the specification.

Many specific details are elaborated in the following description to facilitate the full understanding of the present invention. However, the present invention may also be implemented in other ways different from those described herein. Those skilled in the art can make similar promotions without departing from the content of the present invention, therefore, the present invention is not limited by specific embodiments disclosed below.

Secondly, the term "one embodiment" or "embodiment" here refers to specific features, structures or characteristics that may be included in at least one implementation of the present invention. The phrase "in one embodiment" appearing in different places in the specification does not necessarily refer to the same embodiment, or a separate or selective embodiment that is mutually exclusive with other embodiments.

Embodiment 1

Figure 1:
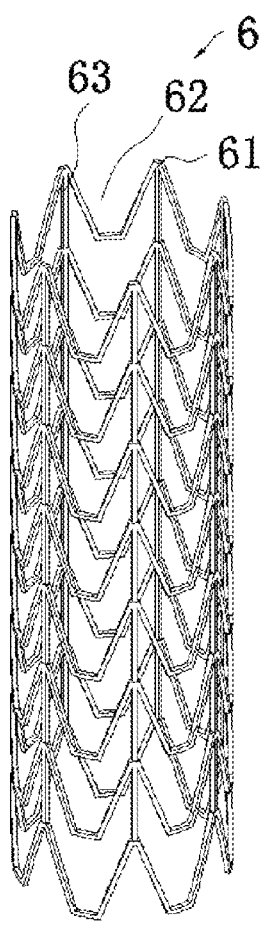
FIG. 1 is a schematic diagram of an overall structure of a left ventricular outflow tract stent.
Figure 2:
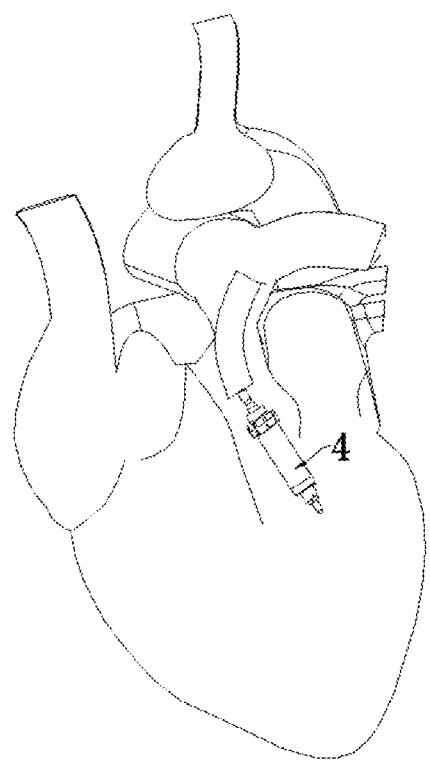
FIG. 2 is a schematic diagram of a state when a stent body is located in the heart.
Figure 3:
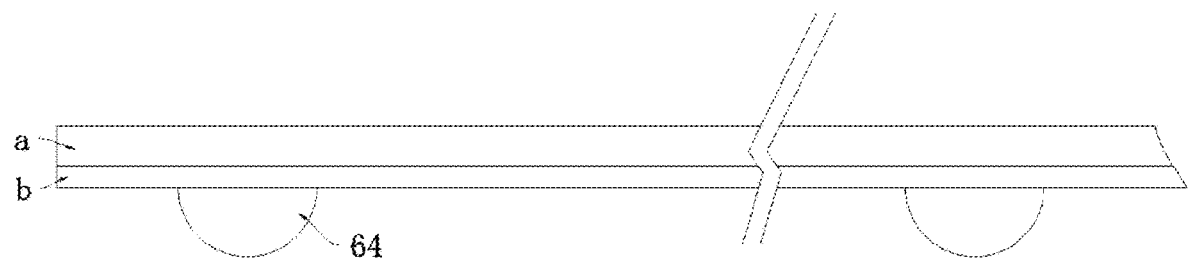
FIG. 3 is a schematic structural diagram of a connecting strip of the left ventricular outflow tract stent.
Figure 4:
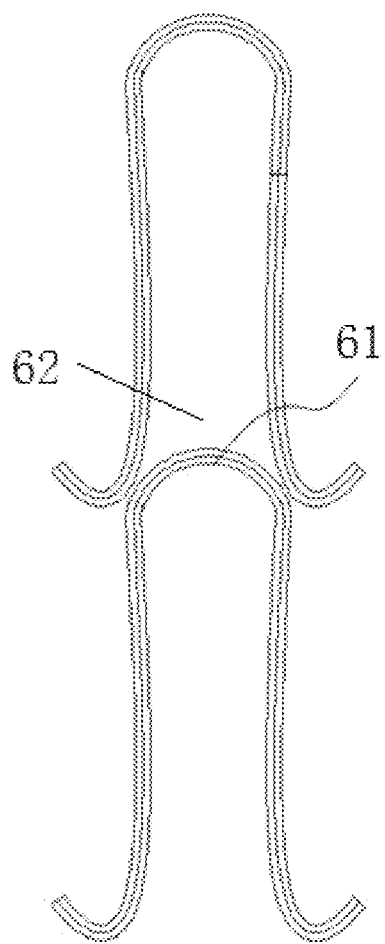
FIG. 4 is a schematic diagram of connection between adjacent supporting components of the left ventricular outflow tract stent.

Referring to FIG. 1 to FIG. 4, a first embodiment of the present invention is shown. This in embodiment provides a left ventricular outflow tract stent, including a stent body 6. The stent body 6 is composed of a plurality of supporting components arranged along a first path coinciding with a left ventricular outflow tract path. The supporting components form a ring structure.

Each of the supporting components includes an inverted-V-shaped frame and an inverted-trapezoidal frame. The inverted-V-shaped frames and the inverted-trapezoidal frames are alternately arranged to form peak regions 61 and valley regions 62. The inverted-V-shaped frames and the inverted-trapezoidal frames continuously form a ring closure, so that the supporting components have a compressed state and an expanded state. When the supporting components are in the compressed state, the size of an outer wall of an end surface of each of the supporting components is less than the size of an inner wall of a storage and transportation component. When the supporting components are in the expanded state, the size of an inner wall of the end surface of each of the supporting components is greater than the size of an outer wall of the storage and transportation component. Moreover, the area of the valley regions 62 in the expanded state is greater than the area of the valley regions 62 in the compressed state, thereby effectively supporting the left ventricular outflow tract, enabling the blood to flow more freely, reducing blockage and pressure, and effectively avoiding blood flow obstruction.

Furthermore, in the compressed state, the peak region 61 of one of the supporting components is located in the valley region 62 of an adjacent supporting component. The peak region 61 of one of the supporting components is adjacent to the valley region 62. The inner wall of the valley region 62 exerts pressure to the outer wall of the peak region 61. Thus, the structure of the stent body 6 is more stable in the compressed state, the supporting components have an interaction force, and a single supporting component may not be in the expanded state unexpectedly. Moreover, the inner wall of the valley region 62 exerts pressure to the outer wall of the peak region 61, thereby increasing the friction and structural stability between the supporting components, avoiding the displacement between the supporting components, and ensuring the structural stability.

The left ventricular outflow tract stent further includes connecting strips 63, and the connecting strips 63 are arranged on the supporting components.

The connecting strips 63 are installed on the supporting components. One end of each of the connecting strips 63 is connected to a V-shaped frame of one supporting component, and the other end of each of the connecting strips is connected to a V-shaped frame of an adjacent supporting component. One end of each of the connecting strips 63 is located in the peak region 61, and the other end of each of the connecting strips is located in the valley region 62. As a result, without affecting the contracted state or expanded state of the supporting components, the connecting strips 63 are sequentially connected and integrated with the stent body 6 to facilitate storage and fixation of the stent body 6 through the connecting strips 63.

Specifically, each of the connecting strips 63 is provided with a protrusion 64, and the material of the protrusions 64 is a magnetic metal.

The protrusions 64 are installed on the connecting strips 63, and the material of the protrusions 64 is the magnetic metal, so that the stent body 6 is limited to increase the reliability of storage and fixation of the stent body 6.

The materials of each of the supporting components and each of the connecting strips 63 are both memory metals. Inner layers of each of the supporting components and each of the connecting strips 63 are photo-induced deformation layers b. Outer layers of each of the supporting components and each of the connecting strips are temperature deformation layers a. Each of the photo-induced deformation layer b and a corresponding temperature deformation layer of the temperature deformation layers a are superimposed.

The materials of each of the supporting components and each of the connecting strips 63 are both memory metals, each of the supporting components and each of the connecting strips 63 are divided into inner and outer layers, each of the inner layers is set as the photo-induced deformation layer b, each of the outer layers is set as the temperature deformation layer a, each of the temperature deformation layers a is superimposed on the corresponding temperature deformation layer of the photo-induced deformation layers b, and the inner layers are closer to the storage and transportation component. When the supporting components are released into the blood, the temperature of the blood causes the temperature deformation layers a to rapidly expand, and at the same time, the photo-induced deformation layers b are illuminated. The photo-induced deformation layers b support the rapid expansion and deformation of the temperature deformation layers a to promote more stable expansion of the supporting components and the connecting strips 63, and the photo-induced deformation layers b and the temperature deformation layers a cooperate with each other. When there is a problem with the expansion of the photo-induced deformation layers b or the temperature deformation layers a in some regions, because another safe deformation layer can expand, the entire supporting components can be in an expanded state to avoid surgical accidents.

Embodiment 2

Figure 5:
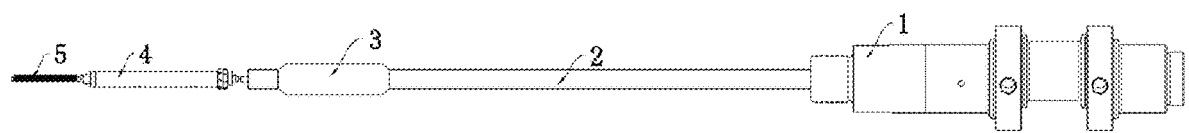
FIG. 5 is a schematic structural diagram of delivering a stent by a delivery system of the left ventricular outflow tract stent.
Figure 6:
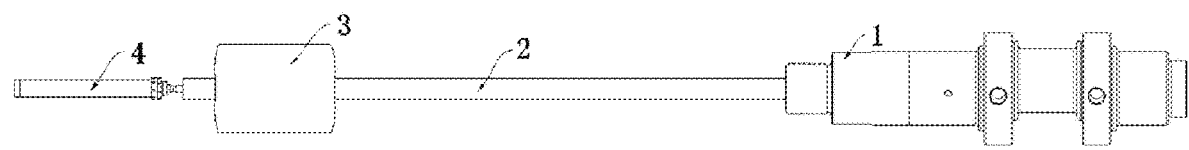
FIG. 6 is a schematic diagram of an expanded state of an air bag component of the delivery system of the left ventricular outflow tract stent.
Figure 7:
FIG. 7 is a schematic diagram of a contracted state of the air bag component of the delivery system of the left ventricular outflow tract stent.
Figure 8:
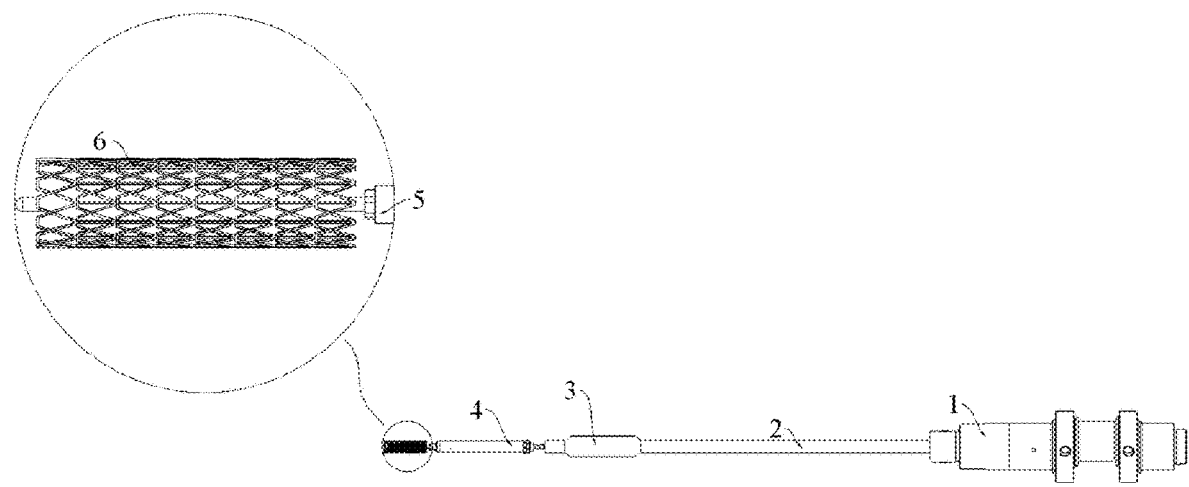
FIG. 8 is a schematic diagram of a contracted state of the air bag component of the delivery system of the left ventricular outflow tract stent.
Figure 9:
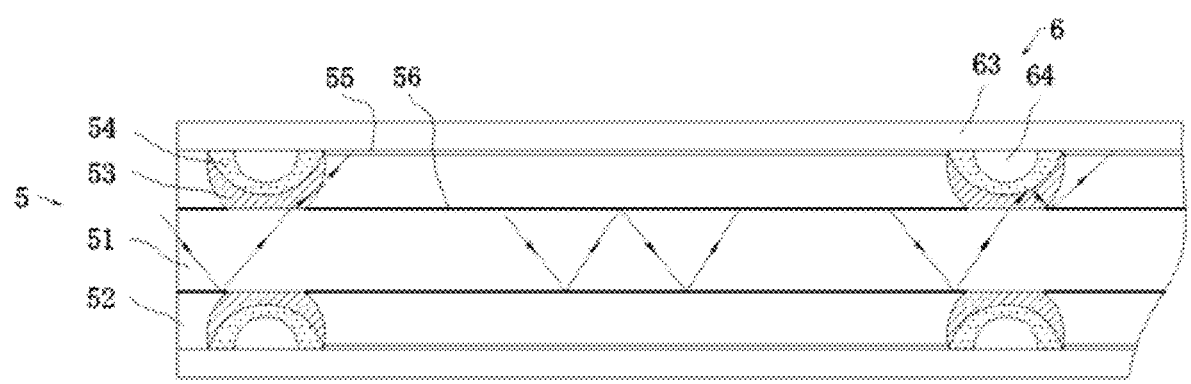
FIG. 9 is a schematic structural diagram of a loading component of the delivery system of the left ventricular outflow tract stent.
Figure 10:
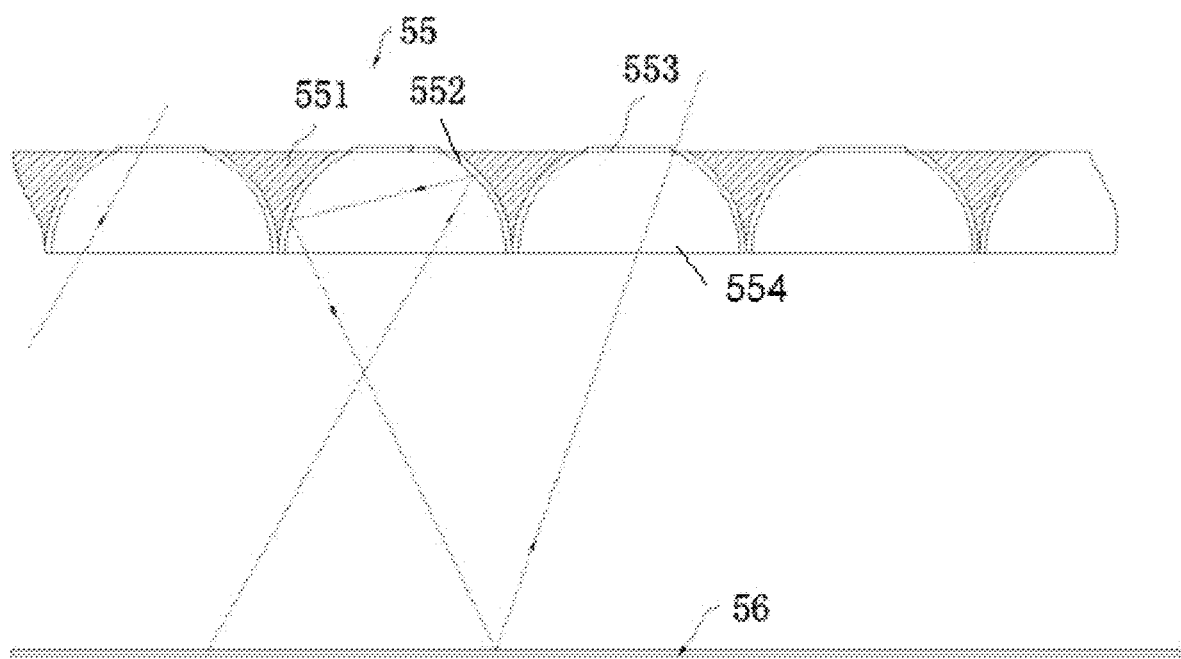
FIG. 10 is a schematic structural diagram of a second reflecting component of the delivery system of the left ventricular outflow tract stent.

Referring to FIG. 1 to FIG. 10, a second embodiment of the present invention is shown. This embodiment provides a delivery system using the left ventricular outflow tract stent, including a control component 1, a delivery catheter 2, an air bag component 3, a guide component 4, and a loading component 5. The control component 1 is configured to control the entire delivery system. The air bag component 3 is connected with the control component 1 through the delivery catheter 2 to control the contraction and expansion of an air bag. The guide component 4 is arranged at an end of the air bag component 3 away from the delivery catheter 2, and the loading component 5 is arranged at an end of the guide component 4 away from the air bag component 3.

The delivery system is mainly composed of the control component 1, the delivery catheter 2, the air bag component 3, the guide component 4, and the loading component 5. The control component 1 is configured to control the entire delivery system. The air bag component 3 is connected with the control component 1 through the delivery catheter 2. Before use, it is necessary to detect whether the delivery catheter 2 is unobstructed. One end of the delivery catheter 2 is connected with an air inflation component and an air discharge component on the control component 1, and the other end of the delivery catheter is connected with the air bag component 3. The air inflation component acts on the air bag component 3 to enable the air bag component to be in the expanded state, and the air discharge component acts on the air bag component 3 to enable the air bag component to be in the contracted state, so that the air bag component 3 adapts to different left ventricular morphologies. During the operation, the air bag component 3 preliminarily expands the installation position of the stent in the left ventricle to prevent surgical accidents caused by the tissue force between left ventricular regions affecting the expansion of the stent, so that the stent can be released more safely. The guide component 4 is installed at the end of the air bag component 3 away from the delivery catheter 2 to guide the stent. The loading component 5 is installed at the end of the guide component 4 away from the air bag component 3 for storage and carrying of the stent body 6.

Specifically, the loading component 5 includes an optical channel 51, a first reflecting component 56, a second reflecting component 55, and a first medium component 53. The optical channel 51 is arranged on the guide component 4. A light source is arranged in the optical channel 51 and acts in the optical channel 51. The first reflecting component 56 is arranged at the periphery of the optical channel 51 and surrounds the optical channel 51. First light-pervious regions are alternately arranged on a surface of the first reflecting component 56. The second reflecting component 55 is arranged at the periphery of the first reflecting component 56. A first gap 52 is formed between the second reflecting component 55 and the first reflecting component 56. The first medium component 53 is arranged in the first gap 52. The position of the first medium component 53 corresponds to the first light-pervious regions.

The optical channel 51 is installed at the end of the guide component 4 away from the air bag component 3. An optical path is formed in the optical channel 51. The material of the optical channel 51 has relatively high transparency and stability to ensure that light can pass through. The material used for the optical channel 51 may be acrylics, optical fiber, light guide fiber, or other materials capable of transmitting light. The light source is arranged in the optical channel 51 and acts in the optical channel 51. The light source may be an LED lamp. The first reflecting component 56 is installed at the periphery of the optical channel 51. The first reflecting component 56 surrounds the entire optical channel 51 and continuously reflects the light in the optical channel 51. First light-pervious regions are alternately arranged on the surface of the first reflecting component 56, so that the light is refracted to the outside of the first reflecting component 56 through the first light-pervious regions. The second reflecting component 55 is installed at the periphery of the first reflecting component 56. The second reflecting component 55 is a semi-transparent and semi-reflective layer. A part of the light passing through the first light-pervious regions passes through the second reflecting component 55 and acts on the stent body 6, and another part of the light is also repeatedly refracted through the second reflecting component 55 and acts on the stent body 6. The first gap 52 is formed between the second reflecting component 55 and the first reflecting component 56. The medium in the first gap 52 may be air or a light-pervious filler for supporting the second reflecting component 55. The first medium component 53 is installed in the first gap 52 to provide certain support for the stent body 6. The refractive index of the first medium is greater than the refractive index of the optical channel 51, so that a falling point of a refracted optical path on the second reflecting component 55 faces a direction away from the first light-pervious regions. By means of processing of the first medium component 53, a light emitting angle can be expanded to prevent excessive light from being blocked, thereby avoiding inability to illuminate the surface of the stent body 6. The position of the first medium component 53 corresponds to the first light-pervious regions, so that the first medium component 53 is capable of performing secondary refraction on the light refracted from the first light-pervious regions to enable the light to uniformly act on the photo-induced deformation layers b.

Further, the side of the first medium component 53 away from the first light-pervious regions is provided with a magnetic concave layer 54 matched with the protrusion 64, and the magnetic concave layer 54 adsorbs the protrusion 64 to maintain the stability of the contracted state of the stent body 6, prevent accidental expansion of the stent body 6 under the action of external forces, and better fix the stent body 6. It should be noted that the magnetic attraction force between the magnetic concave layer 54 and the protrusion 64 is smaller than the expansion force caused by the deformation of the stent body 6 and the connecting strips 63 under the influence of light and temperature, thereby preventing the stent body 6 and the connecting strips 63 from being unable to expand. The side of the magnetic concave layer 54 close to the first medium component 53 is provided with a reflecting surface to refract the light refracted onto the first medium component 53 again, thereby increasing the utilization efficiency of the light.

The second reflecting component 55 includes a first medium layer 551 and a reflecting cover 552. The reflecting cover 552 is arranged on a side of the first medium layer 551 close to the optical channel 51. The reflecting cover 552 is provided with a light inlet end 554 and a light outlet end 553, and the size of the light inlet end 554 is greater than the size of the light outlet end 553.

The second reflecting component 55 is composed of the first medium layer 551 and the reflecting cover 552. The reflecting cover 552 is embedded on the side of the first medium layer 551 close to the optical channel 51 for refraction of light. The reflecting cover 552 is provided with the light inlet end 554 and the light outlet end 553, and the size of the light inlet end 554 is greater than the size of the light outlet end 553. The first medium layer 551 does not block the light inlet end 554 and the light outlet end 553 of the reflecting cover 552. The light at some angles may enter the reflecting cover 552 without contacting the side wall of the reflecting cover 552, and is refracted directly through the light outlet end 553. The light at other angles enters the reflecting cover 552 and then is reflected through the inner wall of the reflecting cover 552, the light is reflected to the surface of the first reflecting component 56, and then, the first reflecting component 56 performs secondary reflection on the light until the light may enter the surface of the stent body 6 from the light outlet end 553 to extend the optical path of the light, thereby extending the range of the light acting on the stent body 6 to enable the light refracted onto the second reflecting component 55 to better act on the stent body 6.

A side wall of a reflecting cavity of the reflecting cover 552 is arranged in an arc shape to better refract light. The light outlet end 553 of the reflecting cover 552 is provided with a diffusion particle layer, and the diffusion particle layer covers the light outlet end 553 to form micro-scale concave-convex surfaces. These concave-convex surfaces can cause the incident light to refract to achieve an effect of light diffusion, thereby preventing the light from focusing at a fixed position.

During use, a doctor places the stent body 6 onto the loading component 5, then preliminarily expands the installation position of the stent in the left ventricle through the control component 1 and the air bag component 3, then controls the loading component 5 to carry the stent to a proper installation position, and finally operates the control component 1 to control the light source to emit light. The supporting components expand from a compressed state to an expanded state to enable the stent body 6 to expand at a correct position to support the left ventricular blood vessels, thereby enabling the blood to flow more freely, reducing blockage and pressure, and effectively avoiding blood flow obstruction.

It should be noted that the above embodiments are merely used for describing the technical solutions of the present invention, but are not intended to limit the present invention. Although the present invention is described in detail with reference to preferred embodiments, those of ordinary skill in the art should understand that modifications or equivalent replacements made to the technical solution of the present invention should be included in the scope of claims of the present invention as long as they do not depart from the spirit and scope of the technical solution of the present invention.

What is claimed is:

1. A system comprising a left ventricular outflow tract stent and a delivery system, wherein the left ventricular outflow tract stent comprises a stent body, the stent body is composed of a plurality of supporting components arranged along a first path configured to coincide with a left ventricular outflow tract path, and the supporting components form a ring structure;

each of the supporting components individually comprises one of both an inverted-V-shaped frame and an inverted-trapezoidal frame, and the inverted-V-shaped frames and the inverted-trapezoidal frames of all of the supporting components are alternately arranged to form peak regions and valley regions;

the left ventricular outflow tract stent further comprises connecting strips, and the connecting strips are arranged on the supporting components for storage and fixation of the stent body;

the delivery system using the left ventricular outflow tract stent comprises a control component, a delivery catheter, an air bag component, a guide component, and a loading component, the control component is configured to control the entire delivery system, the air bag component is connected with the control component through the delivery catheter to control the contraction and expansion of an air bag, the guide component is arranged at an end of the air bag component away from the delivery catheter, and the loading component is arranged at an end of the guide component away from the air bag component for storage and carrying of the stent body; and the loading component comprises an optical channel, a first reflecting component, a second reflecting component, and a first medium component, the optical channel is arranged at the end of the guide component, a light source is arranged in the optical channel and acts in the optical channel, the first reflecting component is arranged at the periphery of the optical channel and surrounds the optical channel, first light-pervious regions are alternately arranged on a surface of the first reflecting component, the second reflecting component is arranged at the periphery of the first reflecting component, a first gap is formed between the second reflecting component and the first reflecting component, the first medium component is arranged in the first gap, and the position of the first medium component corresponds to the first light-pervious regions.

2. The system comprising a left ventricular outflow tract stent and a delivery system according to claim 1, wherein each of the connecting strips is provided with a protrusion, and a material of the protrusions is a magnetic metal.

3. The system comprising a left ventricular outflow tract stent and a delivery system according to claim 2, wherein a side of the first medium component away from the first light-pervious regions is provided with a magnetic concave layer matched with a respective protrusion, and a side of the magnetic concave layer close to the first medium component is provided with a reflecting surface.

4. The system comprising a left ventricular outflow tract stent and a delivery system according to claim 1, wherein materials of each of the supporting components and each of the connecting strips are both memory metals, inner layers of each of the supporting components and each of the connecting strips are photo-induced deformation layers, outer layers of each of the supporting components and each of the connecting strips are temperature deformation layers, and each of the photo-induced deformation layers and a corresponding temperature deformation layer of the temperature deformation layers are superimposed.

5. The system comprising a left ventricular outflow tract stent and a delivery system according to claim 1, wherein the second reflecting component comprises a first medium layer and a reflecting cover, the reflecting cover is arranged on a side of the first medium layer close to the optical channel, the reflecting cover is provided with a light inlet end and a light outlet end, and the size of the light inlet end is greater than the size of the light outlet end.

6. The system comprising a left ventricular outflow tract stent and a delivery system according to claim 5, wherein a side wall of a reflecting cavity of the reflecting cover is arranged in an arc shape.

7. The system comprising a left ventricular outflow tract stent and a delivery system according to claim 5, wherein the light outlet end of the reflecting cover is provided with a diffusion particle layer.

* * * * *